United States Patent [19]

Sherman et al.

[11] Patent Number: 5,735,280
[45] Date of Patent: Apr. 7, 1998

[54] ULTRASOUND ENERGY DELIVERY SYSTEM AND METHOD

[75] Inventors: Marshall L. Sherman, Cardiff; Thomas M. Castellano, Temecula, both of Calif.

[73] Assignee: Heart Rhythm Technologies, Inc., Temecula, Calif.

[21] Appl. No.: 708,829

[22] Filed: Sep. 9, 1996

Related U.S. Application Data

[63] Continuation-in-part of Ser. No. 434,004, May 2, 1995, Pat. No. 5,606,974.

[51] Int. Cl.$^6$ .................................................. A61B 8/00
[52] U.S. Cl. .................... 128/600.03; 601/2; 607/97
[58] Field of Search .................. 128/660.01, 660.02, 128/660.03, 660.06; 601/2, 3; 607/105, 102, 113, 116, 97; 604/22

[56] References Cited

U.S. PATENT DOCUMENTS

| | | | |
|---|---|---|---|
| 4,706,681 | 11/1987 | Breyer et al. | 128/642 |
| 5,295,484 | 3/1994 | Marcus et al. | 128/660.03 |
| 5,304,214 | 4/1994 | DeFord et al. | 607/105 |
| 5,431,664 | 7/1995 | Ureche et al. | 606/128 |
| 5,447,509 | 9/1995 | Mills et al. | 606/1 |
| 5,456,682 | 10/1995 | Edwards et al. | 606/31 |

*Primary Examiner*—George Manuel
*Attorney, Agent, or Firm*—Fulwider Patton Lee & Utecht, LLP

[57] ABSTRACT

An energy delivery system and method controls the frequency of the power driving an ultrasonic device to achieve more efficient power delivery. During operation of the ultrasonic device to deliver power to a patient site, the system and method automatically sweeps the drive power through a frequency range, locates the series and parallel resonance frequencies, calculates the average of those frequencies and locks the power generator at that average frequency to drive the crystal. This frequency sweep procedure occurs automatically when the ultrasonic crystal is located at the patient site and the power generator operator presses the power-on switch to apply power. The method of tuning the power generator thus occurs when the crystal is at the site temperature and is transparent to the operator. The application of an external bio-layer to the crystal increases its bandwidth and its robustness. Mounting a temperature sensor or sensors at the crystal permits monitoring of the crystal temperature and allows drive level control over the power generator to control the temperature at the crystal.

32 Claims, 9 Drawing Sheets

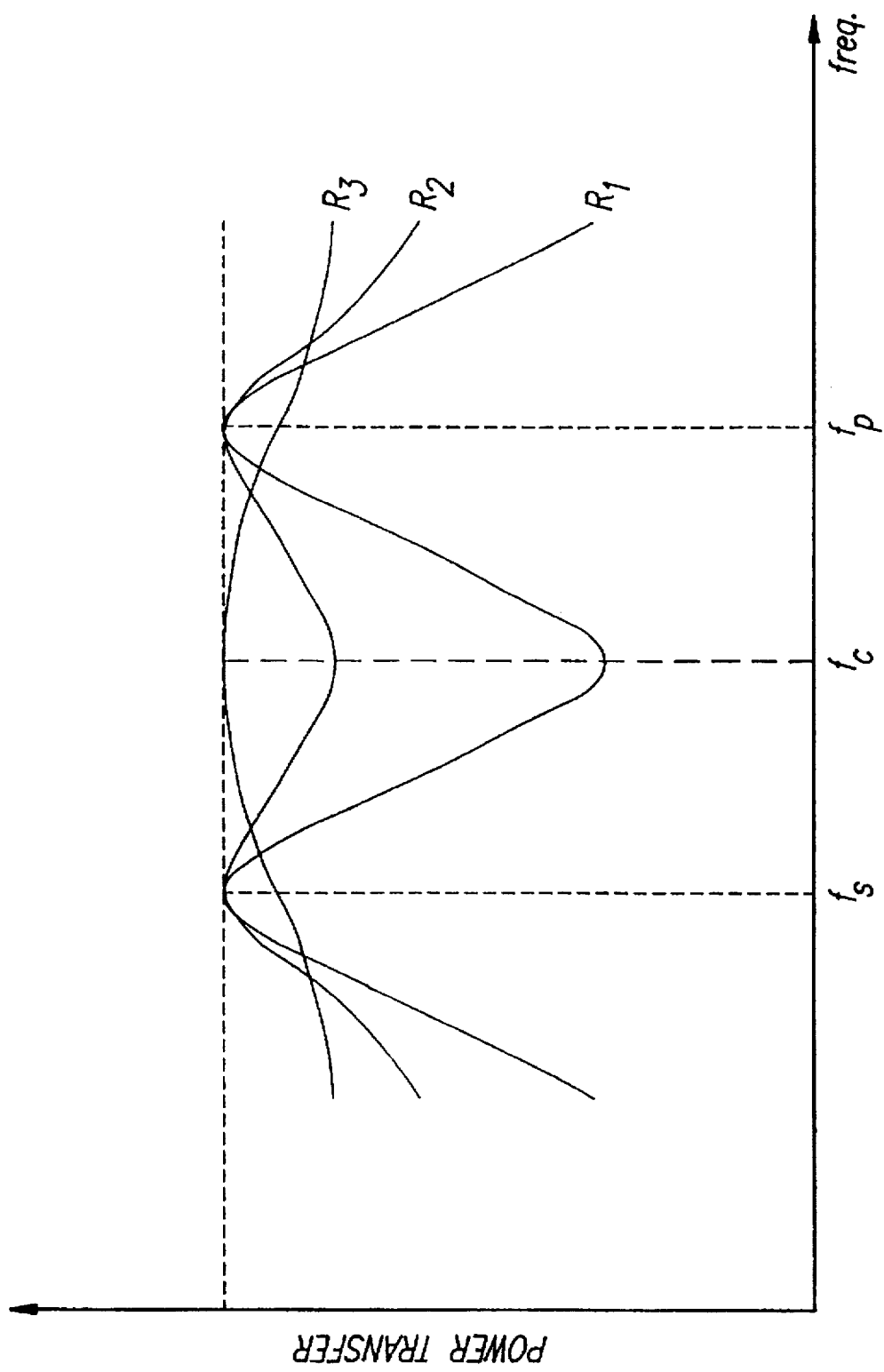

ULTRASOUND ENERGY DELIVERY SYSTEM AND METHOD

The application is a continuation-in-part application of Ser. No. 08/434,004, filed May 2, 1995, now U.S. Pat. No. 5,606,974.

BACKGROUND

The invention relates generally to power control, and more particularly, to a system and method for the more efficient transfer of energy from an ultrasonic power delivery system to biological tissue.

Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia. Arrhythmia can be controlled in many cases by ablating the errant heart tissue.

Once the origination point for the arrhythmia has been located in the tissue, the physician may use an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

Electrophysiological ("EP") ablation is a procedure more often employed in terminating cardiac arrhythmia. This procedure typically involves applying sufficient energy to the interfering conductive tissue to ablate that tissue, thereby removing the irregular signal pathway.

The distal end of an EP catheter may include mapping electrodes for locating the arrhythmia initiation site as well as an ablation device for performing the ablation procedure on the interfering conductive tissue. In another case, different catheters may be used for mapping and for ablation. One type of device locatable at the distal end of a catheter for delivering ablation energy to biological tissue is an ultrasonic device, such as a piezoelectric transducer or crystal. The piezoelectric transducer, excited by electrical energy to oscillate at ultrasonic frequencies, imparts acoustic energy to the target tissue thereby causing ablation. However, an ultrasonic device is effectively an electrical to ultrasonic transducer and must be driven properly by electrical energy for effective power transfer. Ultrasonic devices incorporating piezoelectric elements are in effect complex circuits that are a combination of resistance, capacitance, and inductance. In such systems, there are one or more frequencies where the total impedance of the circuit will appear purely resistive. These frequencies are referred to as resonant frequencies.

For an electro-mechanical transducer such as a piezoelectric transducer comprising complex circuitry, it has been found that resonant frequencies occur in pairs of relatively closely-spaced frequencies where the impedance is resistive and the phase angle is zero. The first of these frequencies is the so-called series resonant impedance frequency, and the second is the so-called parallel resonant impedance frequency. Typically, the most efficient energy transfer occurs at a resonant frequency. Less energy is lost in the conversion of electrical to acoustic energy and less energy is lost as heat during radiation of the acoustic energy. However, it has been found that typically with ceramic piezoelectric transducers, energy transfer is optimal at a frequency midway between these closely-spaced resonant frequencies and the power factor approaches, or is, one. Depending on the frequency sensitivity, or "Q", of the particular transducer, energy transfer may be greatly reduced when the frequency of the electrical energy applied to the transducer varies from the optimum frequency.

Resonant frequencies can vary substantially between different transducers depending on their physical structure. Additionally, the resonant frequencies of a particular transducer can vary substantially depending on the loading on the transducer at the time. The environmental loading, such as the temperature to which the transducer is exposed, can cause a shift in the resonant frequencies as can changes in the tissue or contact loading on the transducer.

It has been noted that a significant change in the optimal frequency can occur in a transducer when it is first exposed to room temperature (20° C.) and is then introduced to the patient at normal human temperature (37° C.). Calibrating the transducer for the optimal frequency at room temperature thus may result in a frequency far different from the optimal frequency when the transducer is at patient body temperature. This may result in a much lower power factor, less efficient transfer of power to the body tissue, and the need for longer ablation times or increased input power to achieve the desired ablation. Longer ablation times and increased input power are both undesirable. The former is undesirable due to the increased trauma to the patient and the latter due to the increased risk of exposing the patient to higher power levels. Thus it would be desirable to be able to calibrate the transducer at the actual temperature of the site.

During an EP surgical procedure, both the environmental and contact loading on an ablation transducer can vary widely. When the ablation device contacts body tissue, such as interfering conductive tissue in the heart, the loading is increased. The loading varies as the tissue is ablated or otherwise modified during the procedure and the temperature rises. These variations in loading can cause corresponding variations in the transducer's resonant frequencies, thereby causing variations in the efficiency of power transfer. Therefore, it is preferable to have a lower "Q" transducer so that changes in the loading of the transducer during an EP procedure do not cause an unacceptable lowering of the power factor.

A common method of determining resonant frequency is to apply an alternating current to the transducer and compare the resulting phase angle between the voltage applied to the transducer and the current drawn by the transducer. The phase angle equals ninety degrees for purely inductive circuits and minus ninety degrees for purely capacitive circuits. The phase angle equals zero for purely resistive circuits, with the voltage and current being in phase with each other. A phase angle of zero also indicates a resonant frequency of the transducer. However, this method of determining the resonance frequency is undesirable because the instruments required to determine the phase angle between voltage and current are relatively expensive and are less effective at higher frequencies, such as at 10 mHz. Thus a more practical, but accurate, apparatus and method for determining the optimal operating frequency of a transducer while in vivo is desirable. Such apparatus and method should be accurate at higher frequencies as well as relatively inexpensive and simple to manufacture.

Another consideration in the design of ablation devices is the size of the device used. The device must be small enough to be introduced percutaneously into a patient while at the same time, must be large enough to be mounted on a catheter shaft that has room within for the passage of electrical wires and fluid lumens, depending on the application. Making the ultrasonic crystal device too small and too thin results in a fragile device. Such crystals are inherently extremely hard due to their crystalline structure and many times will be damaged by rough treatment. In some cases, those handling a catheter with an ablation crystal mounted on its distal end may drop the distal end of the catheter subjecting the crystal to a sharp shock. If the crystal is too thin, it may crack thereby rendering it unusable. If the crystal is too thick, it will be difficult to introduce it into a patient.

Thus, a need exists to make the ultrasonic crystal smaller but less fragile and at the same time, keep the crystal biologically compatible. Also, the ablation device should have a reasonable coefficient of thermal conductivity so that heat reaching the device during an ablation procedure will be conducted rapidly by the device. Controlling the temperature at the ablation device is important so that blood boiling and tissue coagulation on the device do not occur. Coagulated tissue on the ablation device can cause an over-loading condition and the crystal may actually cease its vibrations if such loading exceeds the device's limit. It would be desirable to put a temperature sensor in the ablation device to monitor the temperature of the device and control the energy provided to the device to hold the temperature within limits. However, if the ablation device does not conduct thermal energy at a rapid rate or uniformly, the device may be hotter in one area than in another. If the temperature sensor is placed in a lower temperature area, higher temperatures causing blood boiling and coagulation at another part of the device may not be detected early enough. Thus, providing a crystal with relatively rapid thermal conductivity, sensing the temperature at the crystal, and controlling the energy supplied to the crystal for ablation are desirable.

Hence, those skilled in the art have recognized a need for an energy delivery system and method that can provide improved energy delivery to biological tissue. Additionally, those skilled in the art have recognized a need for an energy delivery system and method that can determine the optimal operation frequency of a transducer in-vivo relatively inexpensively and simply. Also, those skilled in the art have recognized the need for a system and method that is relatively insensitive to resonant frequency changes in the transducer caused by loading changes during an EP procedure. Furthermore, those skilled in the art have recognized the need for an improved transducer that is less susceptible to breakage due to physical shocks, yet is small enough to be introduced into a patient and which is large enough to house a temperature sensor or sensors. The present invention fulfills these needs and others.

SUMMARY OF THE INVENTION

Briefly and in general terms, the present invention provides a system and a method for applying acoustic energy to biological tissue, comprising a catheter having distal and proximal ends, an ultrasonic transducer that transduces electrical energy into acoustic energy, said transducer having first and second resonance frequencies, said transducer mounted at the distal end of the catheter, a temperature sensor mounted at the distal end of the catheter that senses temperature and provides a temperature sensing signal, a tuning system connected to the ultrasonic transducer providing electrical energy to the transducer and monitoring the transducer's response thereto to determine the first and second resonance frequencies of the transducer, said tuning system providing first and second resonance signals as a result of the determination, and a power supply that provides electrical energy to the ultrasonic transducer at a frequency that is halfway between the first and second resonance frequencies at a drive level dependent on the temperature sensed by the temperature sensor.

In another aspect, the invention provides processing means for calculating a center frequency as an average of the first and second resonant frequencies. In yet more detailed aspects, there is provided a biologically-compatible, non-metallic layer mounted on the outside of the ultrasonic transducer that lowers the frequency sensitivity of the transducer.

In a further aspect related to temperature control, the processor decreases the power drive level when the temperature signal represents a temperature above a predetermined first threshold temperature. Additionally, the ultrasonic transducer is cylindrically shaped and the temperature sensor is mounted in the ultrasonic transducer.

In accordance with another aspect of the invention, the power supply comprises a power application switch wherein the power supply automatically applies test power to the ultrasonic transducer to determine the first and second resonant frequencies and then applies full power as selected at the halfway frequency. Furthermore, the power supply automatically sweeps through a predetermined range of frequencies to determine the first and second resonant frequencies.

In yet another aspect, the power supply system holds the frequency constant while varying the power level to maintain the temperature within a predetermined range.

Other aspects and advantages of the invention will become apparent from the following detailed description and accompanying drawings, illustrating by way of example the features of the invention.

BRIEF DESCRIPTION OF THE DRAWINGS

FIG. 8 is a diagram showing frequency versus power transfer for three ultrasonic transducers having different frequency sensitivities;

DETAILED DESCRIPTION OF THE PREFERRED EMBODIMENTS

Figure 1:
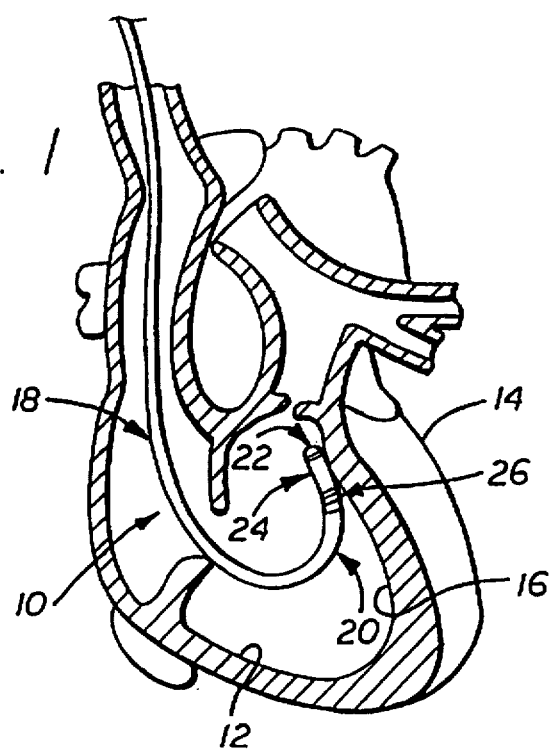
FIG. 1 is a diagrammatic view of a human heart in partial cross section showing an electrophysiological catheter disposed internally and located so that one side of a "side-fire" energy transducer mounted at the catheter's distal end is against the endocardium for performing an electrophysiological procedure.

In the following description, like reference numerals will be used to refer to like or corresponding elements in the different figures of the drawings. Referring now to FIG. 1 in more detail, an electrophysiology ("EP") type catheter 10 is shown inserted into the right ventricle 12 of a human heart 14 for localized diagnosis or treatment of the endocardial tissue 16 thereof. The catheter includes, in this case, an elongated catheter tube or body 18 having a distal end 20 with an electrode 22 mounted at the distal tip, a cylindrical ultrasonic transducer 24, in this case a piezoelectric device, mounted proximal to the tip electrode, and a band electrode 26 mounted proximal to the piezoelectric transducer 24. The electrodes 22 and 26 and the piezoelectric transducer 24 may be individually or simultaneously actuated to perform various electrophysiological procedures. In FIG. 1, the distal end of the catheter is shown parallel to and in contact with the endocardium for performing a "side-fire" EP ablation procedure with the piezoelectric transducer 24.

As used herein, a "side-fire" device is one that is mounted such that it conducts energy sideways in relation to the catheter shaft. This would include the transmission of energy in the radial direction. An "end-fire" device is one that is mounted such that is conducts energy at the distal end of the catheter in relation to the catheter shaft. This would include the transmission of energy in the axial direction.

The distal end 20 of the elongated catheter body 18 is steerable and has sufficient torsional and axial rigidity for maneuvering the distal end through the vascular system and to selected sites within the heart chamber. The catheter body 18 is of sufficient length, for instance to allow for a transluminal percutaneous brachial approach to the heart of an adult patient and/or a transluminal percutaneous femoral approach.

Figure 2:
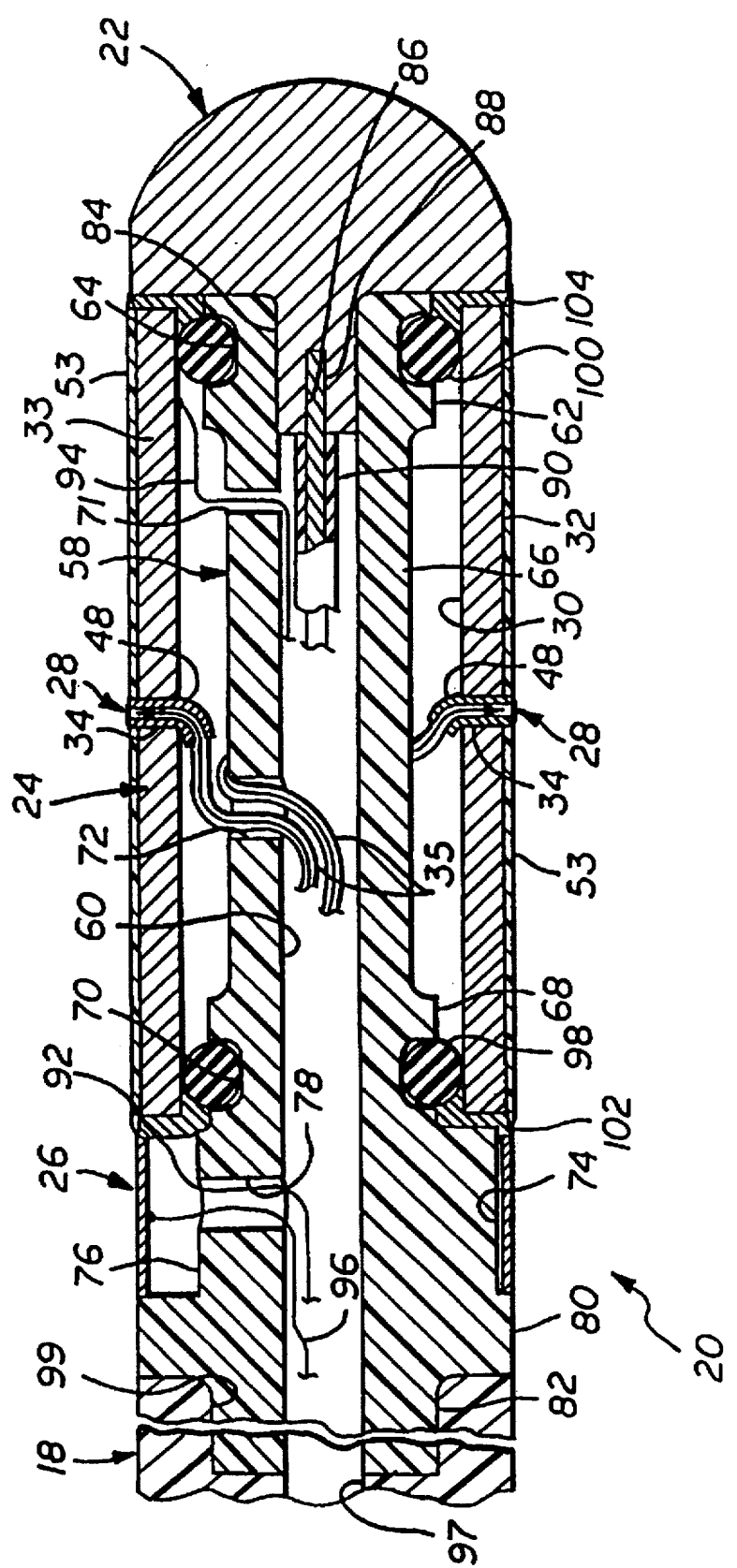
FIG. 2 is an enlarged, partially broken, cross-sectional side view of the distal end of the EP ablation catheter shown in FIG. 1 including a piezo-electric side-fire transducer having a plurality of temperature sensing devices.

Referring now in more detail to FIG. 2, the distal tip electrode 22 may be a mapping type electrode used to send or receive electrical signals from adjacent endocardial tissue for locating aberrant conductive tissues. Suitable materials for the tip electrode 22 include pure platinum, a platinum iridium alloy such as "platinum 10 iridium" (90% platinum 10% iridium), a gold alloy, pure titanium, and/or pure tungsten. The band electrode 26, located proximal to the piezoelectric transducer 24, may also be used either individually or simultaneously with the tip electrode 22 to perform EP mapping procedures.

The cylindrical piezoelectric transducer 24 directs ultrasonic acoustic energy in a radial outward direction for "side-fire" operation. When transmitting ultrasonic energy radially outward, tissue located adjacent the transducer will be ablated.

During an ablation procedure, the piezo-electric transducer or crystal 24 may be subject to overheating if precautions are not taken to control heat buildup. Heat buildup can be prevented by maximizing heat transfer away from the crystal 24. In one embodiment, silver is desired as the outer coating on the crystal. Silver is one of the most thermally conductive materials available, so heat created by ablating the patient is rapidly conducted into the blood flow. However, silver is not as bio-compatible as other materials.

The silver can be coated with gold, which is bio-compatible, but the crystal would be rendered more fragile. In the embodiment shown, the transducer has an exterior coating comprising a biologically-compatible, non-metallic layer 27 mounted on the outside of the ultrasonic transducer. The non-metallic layer 27 serves to protect and strengthen the crystal as well as lowering the frequency sensitivity of the ultrasonic transducer. The thickness of the bio-layer in one embodiment was selected so that the section of catheter having the bio-layer had the same outer diameter as the section of the catheter proximal to the bio-layer.

As shown in FIG. 2, a pair of temperature sensing devices 28 are mounted in the wall of the cylindrical piezoelectric transducer 24. For purposes of illustration, two sensing devices are shown; however, more or fewer sensing devices may be mounted in the transducer. In one particular embodiment, three temperature sensing devices are mounted in the transducer wall and are spaced equi-angularly apart (120 degrees) in a common transverse plane. As is discussed below, having a greater number of temperature sensing devices in the transducer may be more desirable to obtain an accurate temperature indication in a side-fire application.

The cylindrical transducer 24 has inner 30 and outer surfaces 32 and sensor bore holes 34 are formed completely through those surfaces and the wall 33 of the transducer. Each of the sensing devices 28 is in the form of a point sensor mounted within the respective sensor bore hole.

The bore holes 34 may be formed through the wall of the cylindrical piezoelectric transducer by a non-mechanical contact, ultrasonic machining process available commercially. The bore holes, in one embodiment were 0.1778 mm (0.007 in.) in diameter. It is desirable that the temperature sensing devices 28 be as small as possible so that when the devices are mounted in the sensor bore holes of the piezoelectric transducer 24, the transducer's ultrasonic performance is minimally affected and the temperature response times are minimized.

Figure 3:
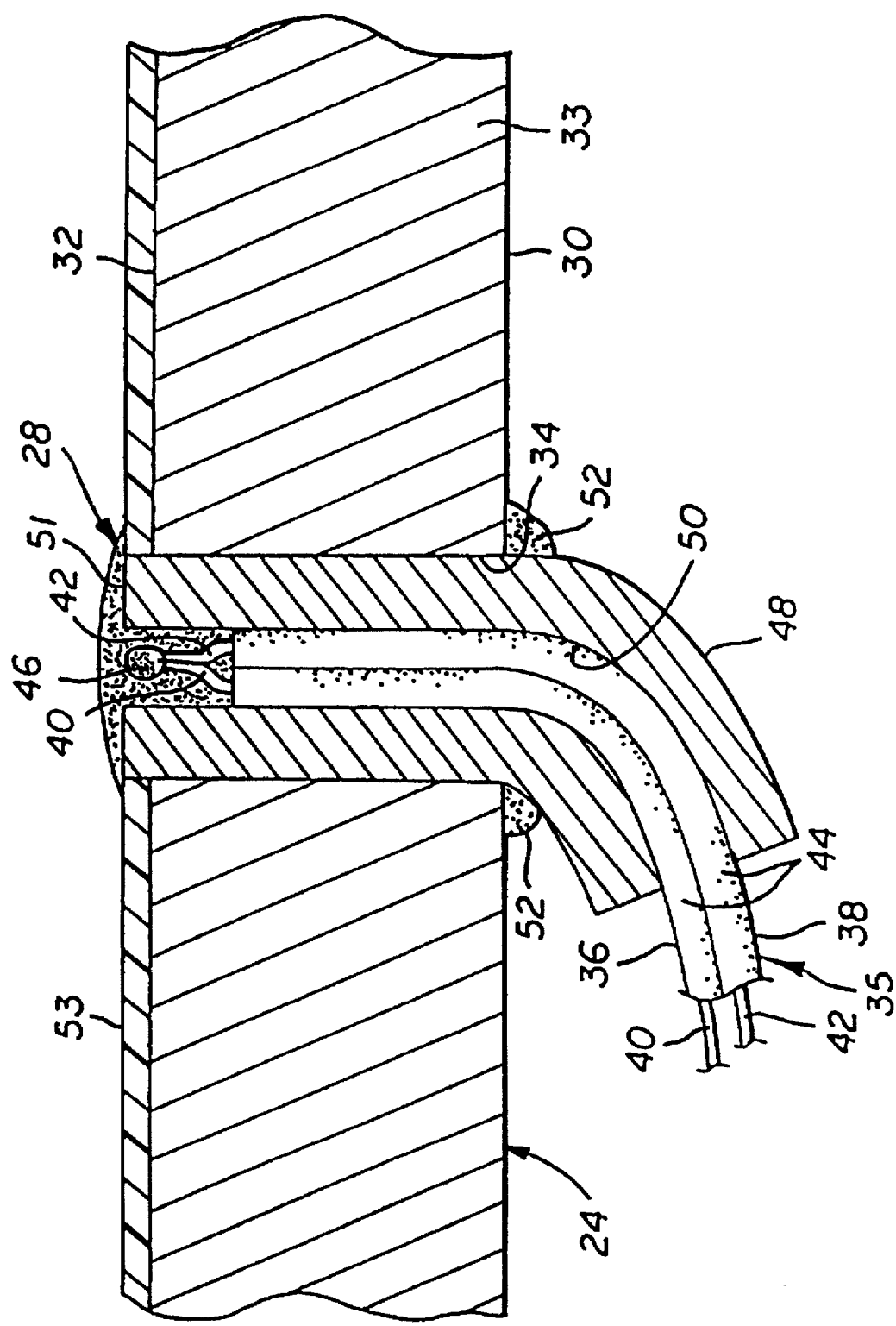
FIG. 3 is an enlarged sectional side view of one of the temperature sensing devices in FIG. 2 showing its mounting configuration in the catheter.

Referring now to FIG. 3, thermocouples 33 used as the temperature sensing device 28 are shown. The thermocouple includes an elongated electrical sensing lead pair 35 comprising individually insulated flexible electrical temperature sensing leads 36 and 38. The electrical leads include respective electrically conductive wires, 40 and 42, formed of dissimilar materials. The distal portion of each wire is stripped of its insulation 44 and is coupled with the stripped distal portion of the other lead to form the thermocouple. In one embodiment, one wire 40 is formed of copper and the other wire 42 is formed of constantan ("T" type). Alternatively, the thermocouple 33 may be constructed of other dissimilar metallic materials.

The distal portions of the dissimilar wires 40 and 42 may be joined such as by welding or bonding together, for instance by conductive solder 46, to form the thermocouple junction along the length of the solder joint. The electrical temperature sensing leads 36 and 38 are formed from a forty-four gauge (AWG) bifilar wire. A bifilar wire of this sort is available from Hudson International of Trenton, Ga. and when connected as shown, it forms a T-type thermocouple 33. Alternatively, the dissimilar metallic wires may be joined by TIG or laser welding to form an enlarged weld bead defining the thermocouple junction.

In both configurations, electrical current may thus pass through the thermocouple junction to create the thermocouple effect. The opposite ends of the respective sensing leads 36 and 38 may be connected to a connector (not shown) mounted on a manipulation handle at the proximal end of the catheter. The sensing leads carry the sensing signals responsive to the temperature sensed at the thermocouple. Those sensing signals may be used by monitoring equipment to derive temperature indications.

In the embodiment shown in FIG. 3, the sensor bore hole 34 is of a uniform diameter along its length. In this embodiment, a flexible elastomeric tubular sheath 48 is provided for receipt within the sensor bore hole, the sheath having an inner bore 50 therethrough. Preferably, the tubular sheath is composed of an elastomeric polyamide having an inner bore 50 diameter sized for snug receipt of the pair of electric sensor leads 36 and 38 and having an outer diameter sized for a snug fit within the sensor bore hole 34.

To assemble the temperature sensing device 28 to the transducer 24 in the embodiment shown in FIG. 3, the sheath 48 is pulled into the sensor bore hole 34 from the outside surface 32 of the transducer. The length of the sheath is greater than the thickness of the wall of the transducer and the non-metallic layer 27 so that an excess length protrudes inwardly from the inner surface 30 of the transducer. The outer surface of the sheath is cut or otherwise positioned such that it is flush with the outer surface of the non-metallic layer 27. An annular bead 52 of an adhesive, such as cyanoacrylate, is applied around the periphery of the sheath along the inner surface of the transducer to secure the sheath thereto. Not only does this bead 52 anchor the sheath in the bore, but it also provides an inner fluid seal to further prevent the entry of body fluids into the interior of the catheter.

The proximal ends of the bifilar sensor leads 36 and 38 are then received through the inner bore 50 of the sheath 48 from the outside of the transducer such that the distal extremity of the thermocouple 33 is positioned substantially at the same level or flush with the outer surface of the non-metallic layer 27 as shown in FIG. 3. Because the sheath extends inwardly past the edge of the bore 34, it provides a strain relief for the sensing thermocouple leads 36 and 38 as well as protecting them from the possible loss of their insulation layers 44 should they scrape against the transducer 24. Movement of the transducer 24 occurs due to the nature of a piezoelectric transducer and such movement can be detrimental to sensor leads.

Thereafter, an adhesive 51 is applied to the thermocouple, sheath, and non-metallic coating 27 to seal and anchor the assembly as one as shown in FIG. 3. A crown allows the thermocouple to be mounted flush with the outer surface of the non-metallic coating 27. The non-metallic coating 27 provides a better acoustical impedance match between the piezoelectric crystal and heart tissue for more efficient energy transfer as discussed below in more detail. The coating 27 also provides a bio-layer and adds mechanical strength to the transducer.

As mentioned above, it has been found that piezoelectric transducers will effect a pumping action of fluid through an associated orifice or opening due to the movement of the transducer. Fluid entry into the interior of an EP catheter is undesirable because it may significantly dampen the piezoelectric transducer's performance rendering the catheter effectively useless. The approach described above and illustrated in the accompanying figures prevents fluid entry. In the embodiment shown in FIG. 3, the use of a resilient sheath 48 compressed in the bore through the piezoelectric transducer 24 provides a first, main defense against leakage. By applying adhesive/sealant about the sheath on the outside and the inside provides further protection against leakage as well as performing other functions described above.

Figure 4:
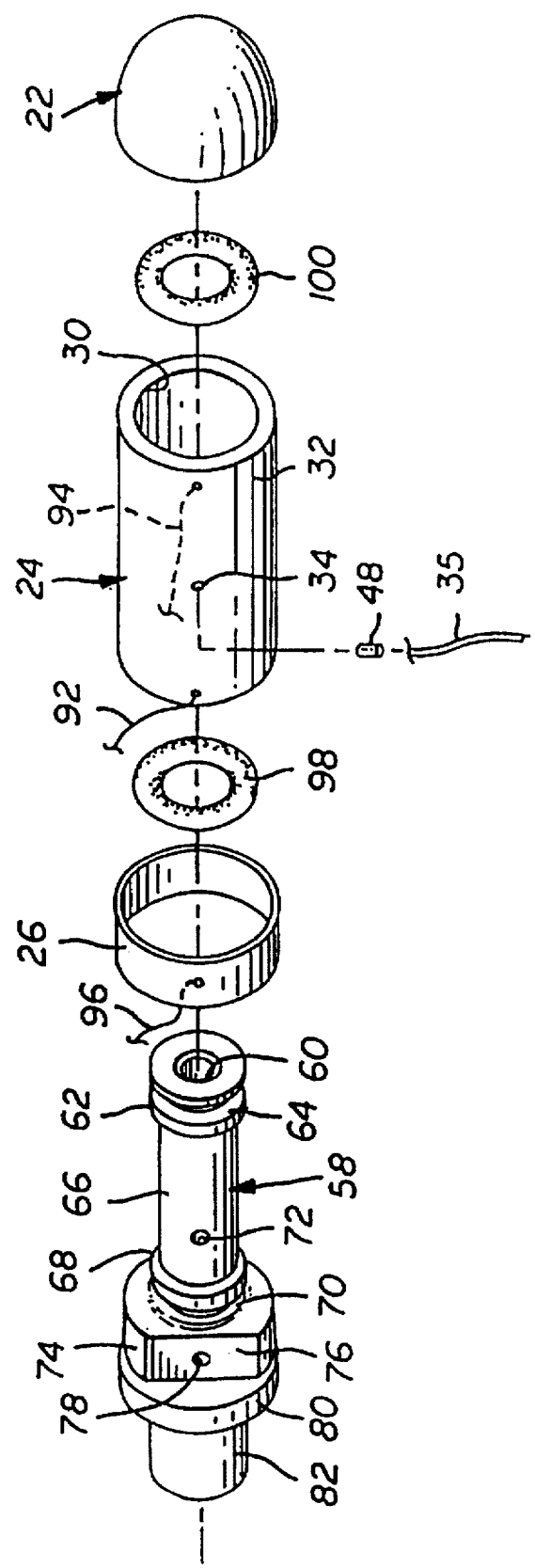
FIG. 4 is an exploded perspective view of the distal end of the EP catheter shown in FIG. 2.

With reference now to FIGS. 2 and 4, the construction of the distal end 20 of the catheter will be described including the assembly of the distal end electrode 22, the cylindrical piezoelectric transducer 24, and the band electrode 26 onto the distal end of the catheter. In general, the distal tip electrode 22, piezoelectric transducer 24, and band electrode 26 are mounted to a mounting member or base 58 and the base is mounted to the distal end of the catheter body 18.

The mounting base 58 is generally an elongated cylindrical body having a longitudinal axial bore 60 therethrough. The distal end of the base has a head 62 formed with an annular O-ring retention groove 64. The base is formed with a smaller diameter neck 66 extending in the proximal direction from the head 62 to a larger diameter flange 68 also formed with an annular O-ring retention groove 70. A radial sensor lead bore 72 is formed through the wall of the neck 66, generally at the medial portion thereof. Formed proximally from the flange 68 is a larger diameter shoulder 74 having a flat surface 76 along one side. The flat surface 76 provides room for a welding joint of an electrical lead to the electrode, as discussed below. An electrode lead bore 78 is formed from the flat surface radially inwardly to the axial bore 60. The shoulder 74, from the proximal end thereof, further expands radially to a larger diameter abutment plate 80 and is formed therefrom with a smaller diameter elongated mounting stem 82 (shown partially broken in FIG. 2). The base 58 is electrically insulative and may be formed of VLTEM for example.

The tip electrode 22, in the embodiment shown in FIGS. 2 and 4, is generally bullet-nose in shape but may take other shapes. The proximal end of the tip electrode 22 is formed with a small diameter, axially projecting mounting post 84 in this embodiment. The proximal end of the post is formed with an axial electrode connector bore 86 for connection to an elongated electrical conductor wire 88 having an insulative jacket 90. The insulative jacket at the distal end of conductor wire 88 is stripped away and the distal tip of the wire conductor 88 is received within the connector bore 86. The conductor is affixed to the tip electrode by crimping the post 84 about the conductor or by soldering the conductor thereto, or by other means. The length of the conductor wire 88 is selected such that the conductor may extend and attach to an electrical connector at a manipulation handle (not shown) at the proximal end of the catheter 10. In the preferred configuration, the conductor wire is formed of a high strength copper beryllium that conducts electrical signals from the tip electrode to the connector at the proximal end of the catheter. In addition, the conductor wire acts as a safety chain to ensure that the tip assembly remains on the catheter shaft while being used in an EP procedure.

The piezoelectric transducer 24 has an outer diameter that is just slightly less than the catheter body 18 and the tip electrode 22 so that the diameter is the same when the non-metallic coating 27 is applied. The transducer 24 may be composed of a ceramic crystalline material. The outer 32 and inner 30 surfaces of the transducer have a thin film, electrically conductive metallic coating (not shown) such as gold, silver, or nickel disposed thereon to provide transducer excitation electrodes. A first electrically conductive transducer wire 92 is soldered to the metallic coating disposed on the outer surface 32 of the transducer at the proximal end thereof. A second electrically conductive transducer wire 94 is soldered to the metallic coating disposed on the inner surface 30 of the transducer at the distal end thereof. Each of the transducer wires has an electrically insulative jacket (not shown) that insulates the respective wires along their lengths to prevent short circuiting.

The band electrode 26 is generally a thin walled ring having an outer diameter substantially the same diameter as the catheter body 18, and the tip electrode 22. The inner diameter of the band is sized for mounting over the shoulder 74 of the base 58. The electrode band is electrically conductive and may be formed of platinum or gold or other materials. An electrical sensor lead 96 is provided and has its distal end bonded to the inner surface of the band, for instance by soldering or weldment. The electrode sensor lead 96 has an electrically insulative jacket (not shown) that insulates the lead along its length.

The catheter body 18 is formed with a longitudinal inner lumen 97 that extends the entire length of the body to its proximal end. The distal extremity of the catheter body is formed with an annular mounting hole 99 having an inner diameter sized for receipt of the mounting stem 84 of the base 58.

When the distal end of the catheter 10 is assembled, the proximal end of the electrode sensor lead 96 of the electrode band 26 is passed inwardly through the electrode lead bore 78 of the base 58 and extended in a proximal direction out through the inner bore 60 thereof. The electrode band is thereafter assembled over the shoulder 74 of the base into contact with the abutment plate 80. The band is adhesively bonded to the shoulder, for instance using epoxy, to securely affix the band electrode to the base.

A pair of elastomeric O-rings 98 and 100 are provided to center the piezoelectric transducer 24 on the mounting base 58 at the catheter distal end and fix it in position. They also vibrationally isolate the piezoelectric transducer 24 from the other components of the catheter 10. The first O-ring 98 is positioned in the second retainer groove 70 of the flange 68 at the proximal end of the neck 66. The second O-ring 100 is disposed within the first retainer groove 64 at the head 62 of the base.

The O-rings 98 and 100 may be composed of a low durometer material such as a silicone based polymer that provides sufficient high frequency vibration isolation characteristics while providing sufficient hardness such that the ultrasonic vibrations generated from the piezoelectric transducer 24 are not unduly damped.

The piezoelectric transducer 24, having the temperature sensing devices 28 mounted thereto, is then mounted to the base 58. The first transducer wire 92 at the distal end of the transducer is received inwardly through the electrode lead bore 78 beneath the electrode band 26 and directed in a proximal direction through the inner bore 60 of the base. The second transducer wire 94 at the distal inner end of the transducer, along with the respective temperature sensor lead pairs 35 of the respective temperature sensing devices 28 are guided inwardly into the sensor lead bores 71 and 72 of the neck 66 of the base 58. The cylindrical transducer 24 is then mounted over the O-rings 98 and 100 and the neck of the base. The proximal end of the transducer is spaced a short distance from the electrode band 26 and an electrically insulative spacer bead 102 (FIG. 2) of adhesive/sealant is applied between the band 26, base 58, and transducer 24 to seal the space between the transducer 24 and the electrode band 26 and affix the transducer 24 in position. The adhesive/sealant is of a low durometer, biocompatible adhesive/sealant and may be composed of a silicone-based polymer having sufficient vibrational isolating and electrical insulating characteristics.

The proximal end of the tip conductor 88 of the tip electrode 22 is then received within the distal end of the inner axial bore 60 of the base 58 and the mounting post 84 of the tip electrode pressed into the distal end of the inner bore 60. An adhesive, such as epoxy, bonds the mounting post within the inner bore 60 of the base. The proximal surface of the tip electrode is spaced a short distance from the distal end of the piezoelectric transducer 24 and a second electrically insulative spacer bead 104 of adhesive/sealant is applied between the tip electrode 22, base 58, and transducer 24 to seal the space between the transducer and the tip electrode affixing the transducer in position. This adhesive/sealant is also a low durometer, bio-compatible material having sufficient vibrational isolating and electrical insulating characteristics. The combination of the two internal O-rings 98 and 100 and the two adhesive spacing and sealing beads 102 and 104 at either end of the piezoelectric transducer optimize the transfer of acoustic energy from the transducer to the tissue.

To complete the assembly of the distal end 20 of the catheter 10, the proximal ends of the temperature sensor lead pairs 35, electrode sensing lead 96, transducer wires 93, 94 and the tip electrode conductor wire 88 are gathered together and directed into the distal end of the inner lumen 97 of the catheter body 18. The mounting stem 82 of the base 58 is pressed into the mounting hole 99 of the catheter body and fixedly securely thereto, for instance by an epoxy adhesive. The proximal ends of the sensing lead pairs, tip electrode conductor wire, electrode sensing lead, and transducer wires 92 and 94 are connected to an electrical connector of a manipulation handle (not shown) at the proximal end of the catheter body. They may be used for operative connection to temperature signal processing, mapping, and ultrasonic ablation operating systems.

The adhesive/sealant beads 102 and 104 provide a liquid seal that prevents blood and other fluids from reaching the underside of the piezoelectric transducer 24 and entering the inner lumen 97 of the catheter body 18. This also protects the various electrically conductive leads and wires contained within the catheter from short circuit by body fluids. Additionally, the adhesive rings electrically insulate the electrode band 26, transducer 24 and tip electrode 22 from each other to prevent short circuiting.

Figure 5:
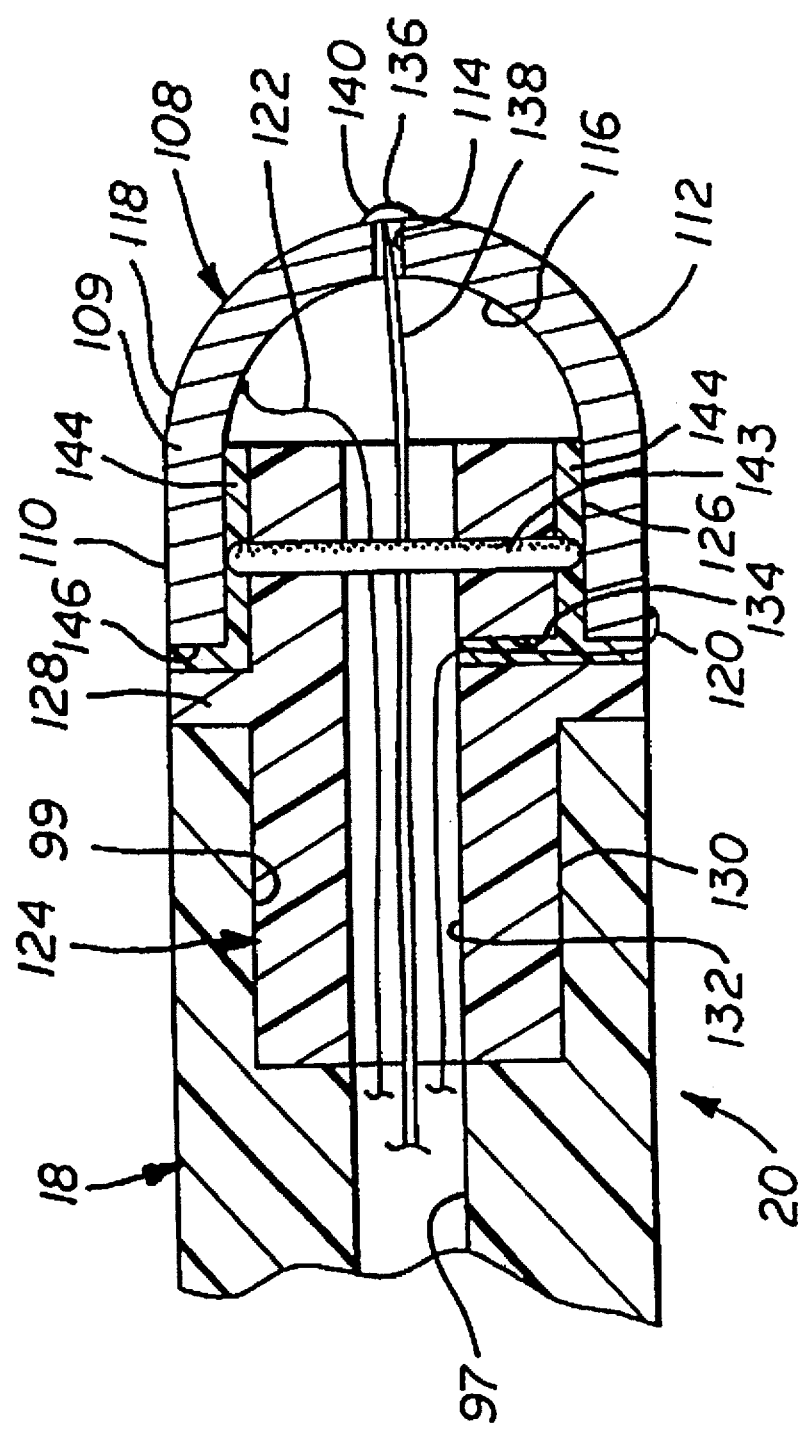
FIG. 5 is an enlarged cross-sectional view of the distal end of another embodiment of an EP catheter in which an "end-fire" ultrasonic transducer is formed with a convex-shaped tip and also includes a temperature sensing device disposed in the transducer.

In the embodiment shown in FIGS. 1, 2, 3, and 4, the transducer 24 is a piezoelectric transducer having a generally cylindrical shape. The cylindrical piezoelectric transducer 24 directs ultrasonic acoustic energy in a radial outward direction for side-fire operation. However, the transducer 24 may take other forms, such as the end-fire configuration shown in FIG. 5. In an alternative embodiment shown in FIG. 5, a piezoelectric transducer 108 is formed in a different configuration. Some reentrant pathways may be located in positions where a side-fire catheter cannot reach. In such cases, an end-fire catheter configuration may be successfully used. Additionally, an end-fire catheter may also be used for more precise ablation procedures where thin but deep lesions are preferred.

In this embodiment, the transducer 108 has a hollow cylindrical portion defining a mounting flange 110 and has an integral, generally hollow, convex-shaped tip to result in a bullet-shaped appearance. The convex tip may be a paraboloid or a hemisphere or other shapes. By having the integral mounting flange 110 as shown, the transducer 108 is easier to mount to the tip of the catheter in comparison to previous designs having only a hemispherical-shaped transducer. Additionally, it can be more accurately and easily mounted on the distal tip because of the larger surface area of the mounting flange and the use of an O-ring 143. This larger surface area for mounting also provides a larger surface area for the application of an adhesive to attach the tip to the catheter shaft. Improved sealing of the inner volume of the transducer should result.

The outer diameter of the flange 110 of the piezoelectric transducer 108 is sized to conform to the outer diameter of the catheter body 18. As shown, the distal-most end of the hemispherical tip 112 of the transducer 108 is formed with an axially aligned sensor bore hole 114. The sensor holes are formed by the ultrasonic machining technique described above.

The inner 116 and outer 118 surfaces of the transducer 108 are plated or coated with an electrically conductive coating (not shown), such as gold, silver, or nickel to provide transducer excitation electrodes.

A first transducer wire 120 is bonded to the metallic coating disposed on the outer surface 118 of the transducer at the proximal end of the mounting flange 110. A second transducer wire 122 is bonded to the metallic coating disposed on the inner surface 116 of the tip 112 of the transducer. The wires are bonded to the respective surfaces by electrically conductive solder or other means to provide electrical continuity. Each of the transducer wires has an electrically insulative jacket (not shown) that insulates the respective wire along its length to prevent short circuiting.

The piezoelectric transducer 108, in this embodiment is constructed for mounting to the distal end 20 of the catheter body 18 through the use of a generally cylindrical mounting member or base 124. In this embodiment, the base has a distally projecting cylindrical mounting neck 126 formed at the proximal end thereof with a larger diameter abutment plate 128. The mounting neck is of smaller diameter than the inner diameter of the transducer flange 110. The outer diameter of the abutment plate 128 is sized to conform to the outer diameter of the catheter body 18. The proximal end of the abutment plate is formed with an axially projecting mounting stem 130 sized for snug receipt within the mounting hole 99 at the distal end of the catheter body 18. The base 124 is also formed with an axial through bore 132 sized substantially the same diameter as the central inner lumen 97 of the catheter body 18. A transducer wire bore hole 134 is formed from the outer surface of the mounting neck to the through bore 132 for receipt of the first transducer wire 120 therein. The base may be composed of an electrically insulative material such as VLTEM.

To assemble the convex piezoelectric transducer 108 onto the distal end 20 of the catheter body 18, a thermocouple sensor 136 such as that shown in FIG. 3 is first formed as described above. The temperature sensor lead pair 138 is directed through the inner lumen of the sheath (not shown) disposed within the axial sensor bore hole 114 of the convex transducer so that the lead pair is disposed within the inner volume of the transducer. The thermocouple end of the lead pair is bonded within the axial sensor bore hole so that the thermocouple is disposed generally flush with the outer surface 118 of the transducer. The thermocouple is bonded within the sensor bore hole using an appropriate adhesive sealant. The adhesive is shaped into a raised mound having a rounded crown 140 slightly above the outer surface of the transducer, the periphery of the crown having a diameter greater that the diameter of the sensor bore hole 114. The adhesive is cured to securely affix the thermocouple 136 in position in relation to the outer surface and the sensor bore hole of the transducer.

Once the adhesive is cured, the crown 140 protects the temperature sensing device 136 from damage and prevents the thermocouple thereof and sensor lead 138 from being pulled inwardly through the sheath after assembly. Furthermore, the adhesive crown 140 permits mounting the thermocouple flush with the outer surface of the transducer and provides a liquid seal that prevents blood and other fluids that may come into contact with the distal end of the catheter from reaching the underside of the piezoelectric transducer 108 through the transducer bore hole 114.

To further assemble the hemispheric piezoelectric transducer 108 onto the distal end 20 of the catheter, the first transducer wire 120 is directed inwardly through the radial transducer wire bore 134 and the second transducer wire 122 and the temperature sensor lead 138 are gathered together and directed through the axial bore 132 of the mounting base 124. An O ring 143 is mounted on the base 124 to center and support the transducer 108 when it is mounted on the base.

The proximal end of the mounting flange 110 of the transducer 108 is then disposed over the mounting neck 126 of the base 124. The O ring assists in disposing the transducer in concentric alignment with the neck 126. Because the inner diameter of the mounting flange is larger than the outer diameter of the mounting neck, adhesive/sealant 144 is applied between the two as well as in the space 146 between the abutment plate 128 of the base and the mounting flange 110. The adhesive/sealant conforms with the outer diameter of the flange 110. The transducer wire bore 134 may also be filled with the adhesive/sealant 144.

The adhesive sealant 144 is of a low durometer, biocompatible polymer that securely affixes the transducer to the mounting neck 126 of the base and has sufficient vibrational isolating and electrical insulating characteristics. The adhesive sealant seals the interior of the catheter body 18 from the entry of bodily fluids that may cause undesirable transducer damping or possible short circuiting.

The respective transducer wires 120 and 122 and the temperature sensor lead 138 are then directed through the inner lumen 97 of the catheter body 18 to the proximal end of the catheter. The mounting stem 130 of the base is then pressed into the mounting hole 99 of the distal end 20 of the catheter body and affixed therein using an appropriate epoxy, for instance. The proximal ends of the sensing leads 138 and transducer wires 120 and 122 are connected to an electrical connector of a manipulation handle connector (not shown) for operative connection to a temperature measurement processing system and transducer operating system.

When the convex transducer 108 is in operation, the adhesive 144 between the mounting flange 110 and the mounting neck 126 provides minimal damping at the hemispherical tip 112 of the transducer because no adhesive is in contact with the inner surface thereof to cause such damping.

Figure 6:
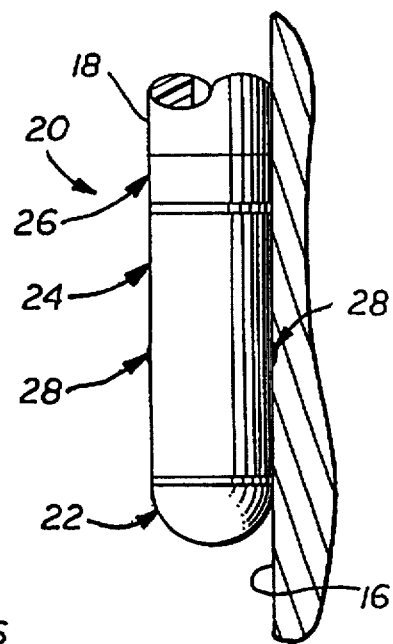
FIG. 6 is a side view of the catheter of FIG. 2 showing its distal end disposed parallel to and in contact with an ablation site for "side-fire" use.

Referring to FIG. 6, a side-fire application of the catheter 10 illustrated in FIGS. 2, 3, and 4 is shown. The distal tip 22 and band electrode 26 may be used for mapping purposes to locate an aberrant endocardial tissue site on the endocardial wall 16 of the heart chamber. Once the site 16 has been targeted, the distal end 20 of the catheter 10 is positioned against the targeted endocardial site 16 in a parallel orientation as shown in FIG. 6 to perform an ablation procedure. For optimum ablation effectiveness, the distal end of the catheter is oriented such that one longitudinal side of the cylindrical piezoelectric transducer 24 contacts the target tissue site. In this orientation, the clinician may activate the piezoelectric transducer to ablate the target endocardial tissue adjacent the transducer.

When activated for ablation, the cylindrical transducer 24 radiates ultrasonic energy at a selected frequency radially outwardly to the endocardial wall 16 to ablate the target tissue. Because there are a plurality of temperature sensors 28 and they are located substantially at the outer surface of the cylindrical transducer, the temperature sensors are able to sense the temperature of the ablated tissue, adjacent flowing blood and the surface temperature of the transducer itself very rapidly. By monitoring sensor outputs or by processing them in other ways, the temperature of the ablation site may be determined.

Figure 7:
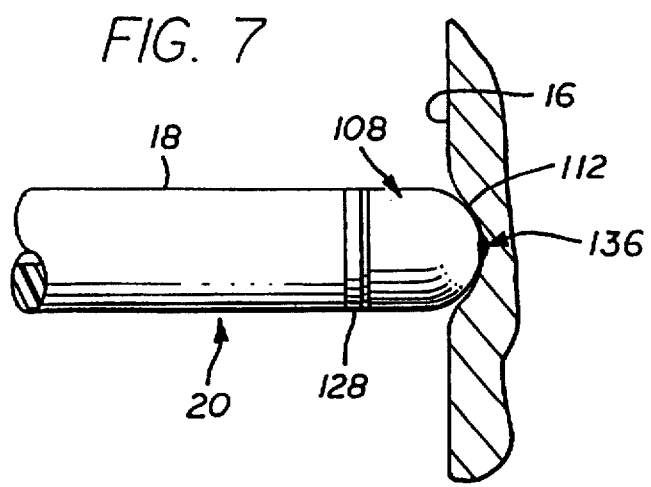
FIG. 7 is a side view of the catheter of FIG. 5 showing its distal end disposed perpendicularly to and in contact with an ablation site for "end-fire" use.

Referring now to FIG. 7 for an end-fire application, the catheter having the hemispherical transducer 108 at its distal tip is illustrated. The hemispherical tip transducer 108 configuration may be useful in certain applications where the aberrant target tissue is located at a position of the heart chamber not conducive to use of the catheter having the cylindrical transducer 24 of FIG. 6. Due to the contours of the heart chamber, the cylindrical transducer may be too large to fully contact the tissue along its longitudinal side and may therefore limit the cylindrical transducer's effectiveness.

In the perpendicular orientation shown in FIG. 7, the tip portion 112 of the convex transducer 108 and the distal tip temperature sensing device 136 are in contact with the target tissue of the endocardial wall 16. In this configuration, the tip transducer 108 is powered to ablate the target tissue. The convex piezoelectric transducer 108 shown may result in a relatively thin but deep lesion. Because the temperature sensing device 136 is in direct contact with the ablated tissue site, a direct indication of the temperature thereof is provided and thus the operation of the transducer may be more precisely and accurately controlled to maintain the temperature within limits.

In either of the catheter configurations shown in the figures, having the temperature sensing devices 28, 136 disposed in sensor bore holes 34, 114 formed in the piezoelectric transducer 24, 108 itself provides a desirable temperature sensing configuration. Because the thermocouple of the sensing device is disposed at the periphery of the transducer, a more accurate and faster temperature sensing response is provided. In addition, the chances of having a sensor in close proximity to the endocardial ablation site provides the clinician with a greater ability to control tissue and blood heating during the ablation procedure minimizing adverse effects to the patient. The temperature sensing devices 28 offer a more rapid temperature sensing response indication of the endocardial ablation site and the flowing blood adjacent the ablation electrode so that ablation procedures can be more accurately and positively controlled.

Furthermore, the mounting means and adhesive/sealant configurations between the distal end of the catheter body and the particular piezoelectric transducer provide a secure mounting arrangement while preventing undesirable leakage of bodily fluids into the catheter body as well as reduced damping of the transducer.

During the ablation procedure, the target tissue is heated, and the resulting heat buildup in the transducer can impair transducer operation. Because of its mass, the target tissue has a greater thermal inertia than the transducer itself. Thus, when power is discontinued to the transducer, its temperature will decrease faster than the temperature of the target tissue. Additionally, at least a part of the transducer is located in the cooler flowing blood that will carry away some of the heat of the transducer. Thus the power to the transducer can be reduced or even shut off, the transducer can be allowed to cool, and the power can be increased or resumed to the transducer before the temperature of the target tissue decreases to any substantial degree. These steps can be accomplished by controlling the drive level of the power generator supplying ablation power to the transducer, as is discussed below in more detail.

FIG. 8 is a representative diagram showing frequency versus power transfer for three ultrasonic transducers R1, R2, and R3. Each transducer has a characteristic frequency or frequencies. The first transducer $R_1$ has a relatively high frequency sensitivity (Q). The series resonant frequency $f_s$ and parallel resonant frequency $f_p$, both of which are characteristic frequencies of this transducer, occur where the power transfer is maximum in this case. The power transfer drops off rapidly to either side of the resonant frequencies as well as in between the resonant frequencies. At the center frequency $f_c$, the power transfer is greatly decreased from both that of the series and parallel resonance frequencies.

For a transducer having a lower frequency sensitivity, such as that shown by $R_2$, there are also two characteristic frequencies, the series resonant frequency $f_s$ and parallel resonant frequency $f_p$ and they still occur where the power transfer is maximum, but the power transfer does not vary as widely at frequencies between $f_s$ and $f_p$. Power transfer still drops off sharply in the region below the series resonant frequency $f_s$ and in the region above the parallel resonant frequency $f_p$. However, in the area between the series and parallel resonant frequencies $f_s$ and $f_p$ including the center frequency $f_c$, the power transfer remains relatively high with only a slight dip at $f_c$.

A transducer having a bio-compatible outer layer that greatly reduces frequency sensitivity (lower Q) is represented by the line $R_3$. For $R_3$, the power transfer is maximum at an operating frequency $f_c$ between the series resonant frequency $f_s$ and parallel resonant frequency $f_p$ and is actually greater than at frequencies $f_s$ and $f_p$, with the power transfer tapering off beyond the region between the series and parallel resonant frequencies. In this case, power transfer is greatest at the frequency $f_c$ midway between the series and parallel resonance frequencies.

Figure 9:
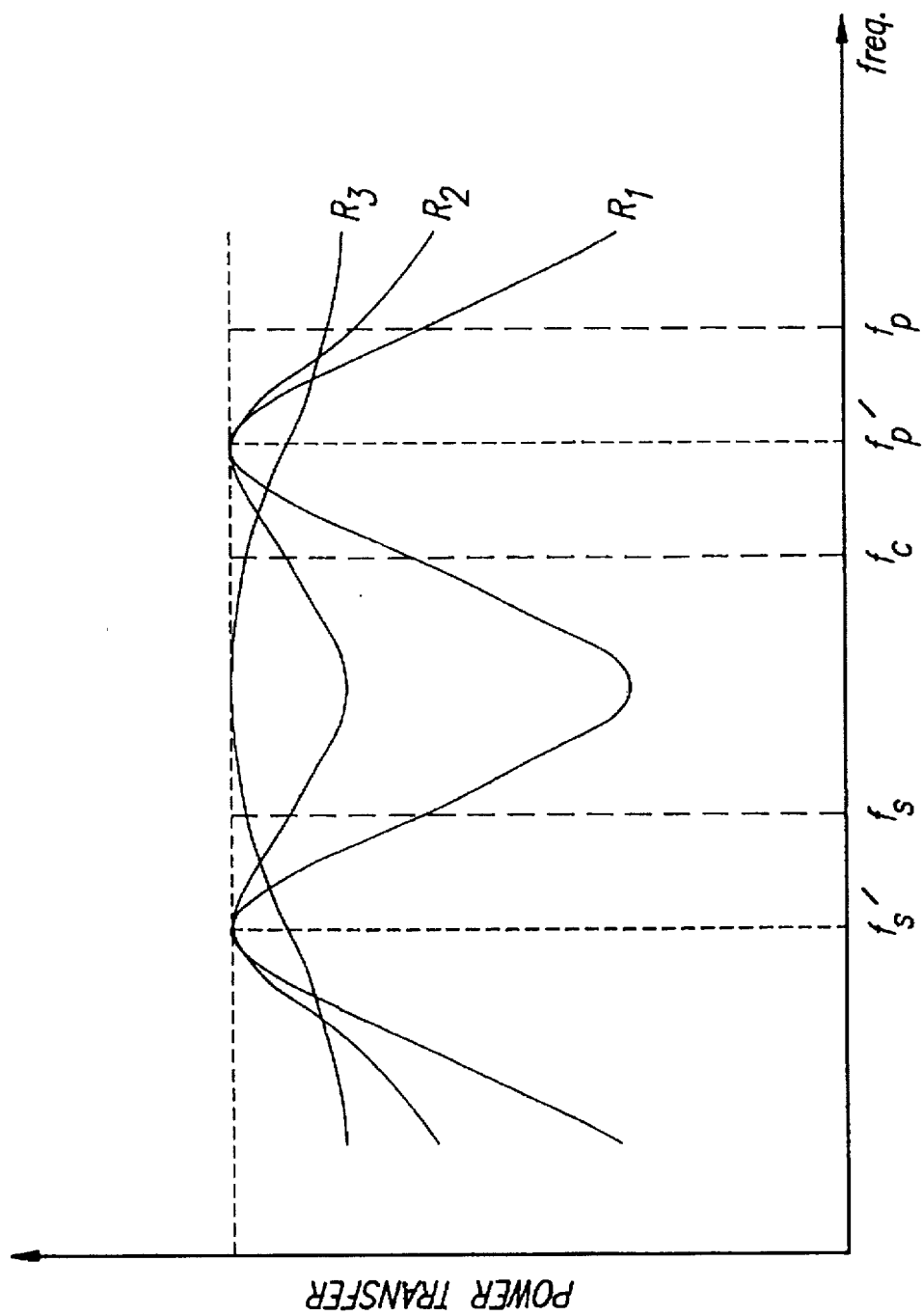
FIG. 9 is a diagram showing shifted frequency versus power transfer curves for the three ultrasonic transducers of FIG. 8 that have undergone a temperature change.
Figure 10:
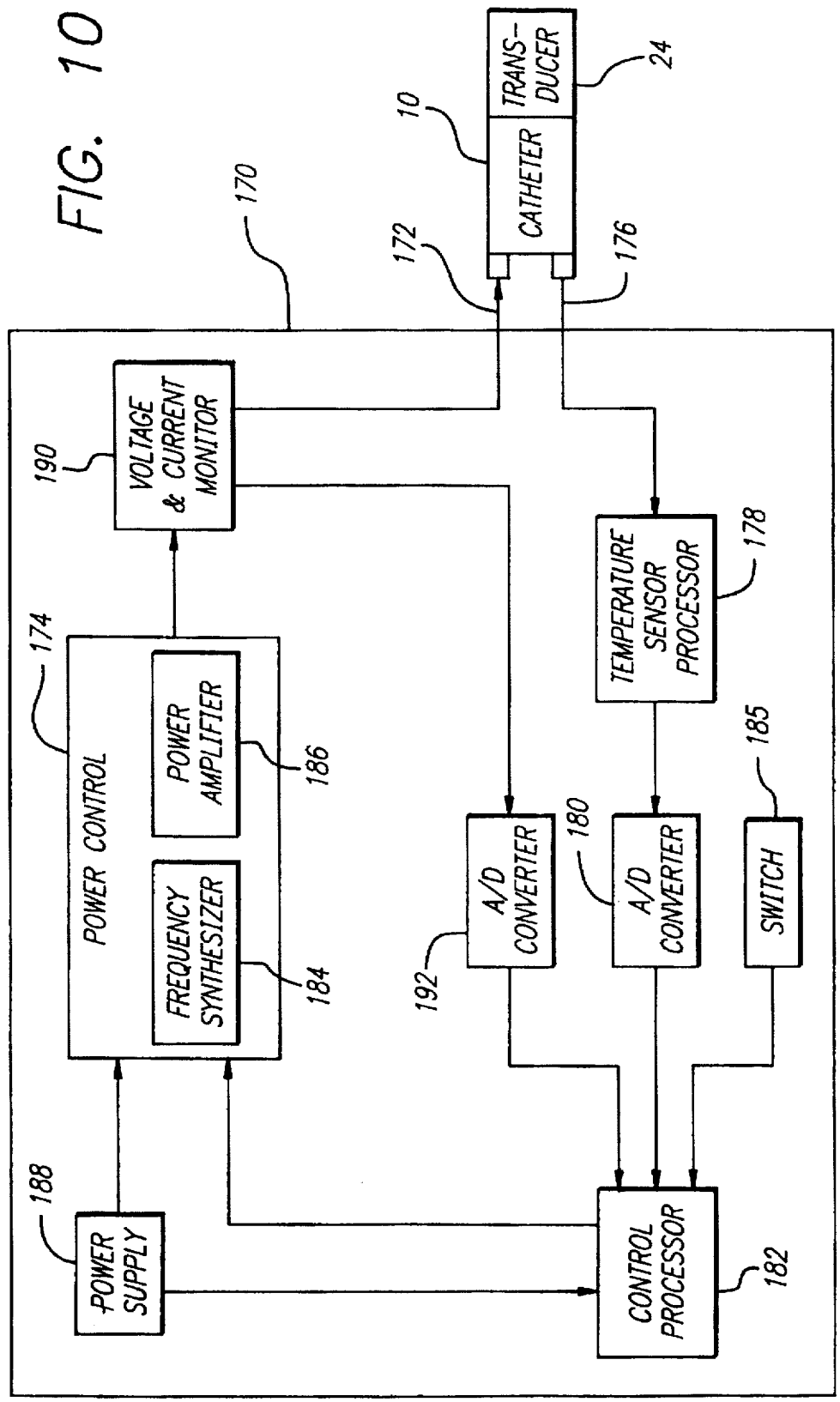
FIG. 10 is a schematic diagram illustrating an ultrasonic energy delivery system for controlling the drive level of an ablation device in accordance with the principles of the present invention.

During the operation of the transducer when subjected to changing temperature and changing loading conditions, the series resonant frequency $f_s$ and parallel resonant frequency $f_p$ will typically drift to some extent, depending on the load applied to the transducer and heat experienced. A shift in the resonant frequencies results in a change in the power transfer curve. For example, the downward shift in the resonant frequencies causes the frequency v. power transfer curves of FIG. 8 to shift to the left, as shown by FIG. 9.

Depending on the particular transducer's frequency sensitivity, even a very small shift in the resonant frequencies (and hence in the power transfer curve) can cause a large change in power transfer. Referring now to FIG. 9, curves for transducers R1, R2, and R3 subjected to different loading conditions than in FIG. 8 are once again plotted on a graph of power transfer versus frequency. In this graph, the original series and parallel resonance frequencies $f_s$ and $f_p$ that are shown in FIG. 8 are now shown in dashed lines. The new series and parallel resonance frequencies $f_s'$ and $f_p'$ are shown and are at lower frequencies. FIG. 9 shows that transducer $R_1$, which has a high frequency sensitivity, experiences a substantial change in power transfer when the resonance frequencies shift. If the frequency of energy driving the transducer were maintained at either of the initial resonant frequencies $f_s$ or $f_p$, the power transfer would substantially decrease when the resonance frequencies shift downward to $f_s'$ and $f_p'$. Transducer $R_2$ also experiences a change in power transfer, although the change is not as great as the change experienced by transducer $R_1$.

For the transducer $R_3$ having an external bio-layer with resulting reduced frequency sensitivity, shifts in the series and parallel resonant frequencies to $f_s'$ and $f_p'$ cause smaller variations in the power transfer curve for an operational frequency at $f_c$ and other frequencies lying between the series and parallel resonant frequencies. By setting and maintaining the operational frequency $f_c$ at a point midway between the original series $f_s$ and parallel $f_p$ frequencies, a small to moderate shift in the series $f_s$ and parallel $f_p$ resonant frequencies will result in a relatively minor change in the power transfer. The power transfer can be held relatively stable as the loading on the transducer changes.

Accordingly, the bio-layer coating 27 is added to the exterior of the ultrasonic crystal to control the frequency sensitivity and achieve results similar to the transducer R3 shown in FIG. 9. In one embodiment, the bio-layer was selected to be 0.03 mm (0.0012 in.) thick. It was found that with a bio-layer of this thickness, an insignificant power transfer change occurred when the operational frequency $f_c$ of the ultrasonic crystal was determined with the ultrasonic crystal at 37° C. and then the crystal was elevated in temperature to 85° C. during an ablation procedure. This bio-layer effectively broadens the bandwidth of the R3 crystal by making it operational over a wider temperature range. As is seen in FIG. 9, the frequency range at which the response varies by an insignificant amount is much broader for R3 than for R1 or R2. The responses for R1 and R2 have dropped much more than for R3.

It was also noted that the bio-layer formed on the external surface of the ultrasonic transducer makes the transducer more durable and less subject to breakage when subjected to shocks during handling. In one embodiment, the bio-layer was formed of 353 ND epoxy made by Epoxy Technologies. The mechanical strength of the crystal is enhanced by the bio-layer with the crystal now being much more robust and can withstand larger impacts without shattering. It was also found that the mentioned epoxy had an acceptable thermal coefficient and transferred heat along the layer at an acceptable rate.

Referring now to FIG. 10, a block diagram of an embodiment of a power generator 170 is presented. The power output line 172 carries the power output from the power control 174 to the transducer 24 at the distal end of the catheter 10 to provide the energy needed for ablation. The temperature input line 176 carries temperature sensor signals from the temperature sensors located at the distal end of the catheter. These temperature sensor signals are processed in the temperature sensor processor 178 which outputs a temperature signal representing the temperature sensed to the control processor 182 through an analog-to-digital ("A/D") converter 180.

The power generator 170 preferably generates a power output having a sine wave. The power controller preferably includes a frequency synthesizer 184 that controls the frequency of the power output. The control processor 182 controls the frequency synthesizer 184 as part of its control of the operation of the power control 174. The power control 174 may include a power amplifier 186 in order to produce the power output 172 needed to be delivered to the catheter 10 for ablation.

The power supply 188 provides power to the various elements of the power generator 170. A power transfer sensor, such as the voltage and current monitor 190, monitors the voltage and current of the ablation energy to determine the impedance presented by the ultrasonic crystal 24. The voltage and current monitor 190 provides signals representing the voltage and current values through an A/D converter 192 to the control processor 182. The control processor 182 controls the frequency synthesizer to alter the frequency driving the ultrasonic crystal 24 until the series and parallel resonant impedance frequencies have been found.

In one embodiment, the control processor 182 automatically causes the frequency synthesizer 184 to sweep through a predetermined frequency range to identify the resonance frequencies of the ultrasonic transducer 24 in response to actuation of the power-on or power application switch 185. At these frequencies, the impedance will be the lowest indicating that maximum power transfer is occurring. The control processor 182 then calculates the average of the series and parallel resonance frequencies and controls the frequency synthesizer 184 to operate at the calculated average frequency.

Specifically in one embodiment, the voltage is held constant as the frequency is swept. The current monitor 190 monitors the current flow to the ultrasonic transducer 24 and provides a current level signal to the processor 182 through the A/D converter 192. The highest current flow indicates the lowest impedance of the ultrasonic transducer. The frequency at which the highest current flow occurs is the series resonance frequency. The lowest current flow indicates the highest impedance of the ultrasonic transducer. The frequency at which the lowest current flow occurs is the parallel resonance frequency. As states above, the processor 182 averages the series and parallel resonance frequencies to arrive at the operating frequency.

In one embodiment, this frequency sweep and operating frequency lock-on procedure was completed in less than one second. A high impedance of 200 Ω was observed with some crystals and a low impedance of 40–50 Ω was observed. An average operating impedance was observed to be 70–80 Ω. The control processor 182 controls the power control 174 to apply power to the transducer 24 at a constant frequency while altering the drive level to maintain the temperature at the transducer within a predetermined range or level.

FIG. 11 is a flow chart illustrating the operation of an energy delivery method in accordance with aspects of the present invention. The catheter having an ultrasonic transducer is introduced into the patient and located at the site where energy is to be delivered. Such may occur for an ablation procedure. During this introduction procedure, the ultrasonic crystal may have stabilized at patient temperature, such as 37° C. The lead for the ultrasonic crystal is plugged into the power generator 170 (FIG. 10) and the physician then causes the power generator to be placed in the "power on" mode 200. The control processor causes the frequency synthesizer to sweep through a range of frequencies to locate the series resonant frequency and the parallel resonant frequency automatically 202. The control processor then averages the two frequencies to determine a center frequency 204. The operational frequency of the instrument is set at the center frequency 206 at which time a predetermined level of power is automatically applied to the transducer for performing the energy delivery process.

The above process is transparent to the user of the system. Pressing the power-on switch causes the system to automatically tune the power to the particular ultrasonic crystal in use at the particular patient temperature to which it has stabilized and then once the tuning is completed, automatically apply power to perform the energy delivery to the patient site. The method and system therefore accurately tune the driving frequency for each crystal and for each energy delivery process. As mentioned above, in one case, the automatic tuning process took less than one second.

A temperature sensor, such as the temperature sensor 28 shown in FIG. 3, is used to sense the temperature at the distal end of the catheter, and the sensed temperature is monitored at step 208 to control the drive level. When the temperature is determined to be above a first selected temperature, such as 85° C. 210, the drive level of the power output is decreased 212 to allow the transducer to cool down. If the temperature is determined to be below a second selected temperature 214, the drive level is increased 216 to a higher level to apply more power to the ablation site. The first and second temperatures may be identical or the second temperature may be below the first by some amount, depending on the desired temperature sensitivity.

Figure 11:
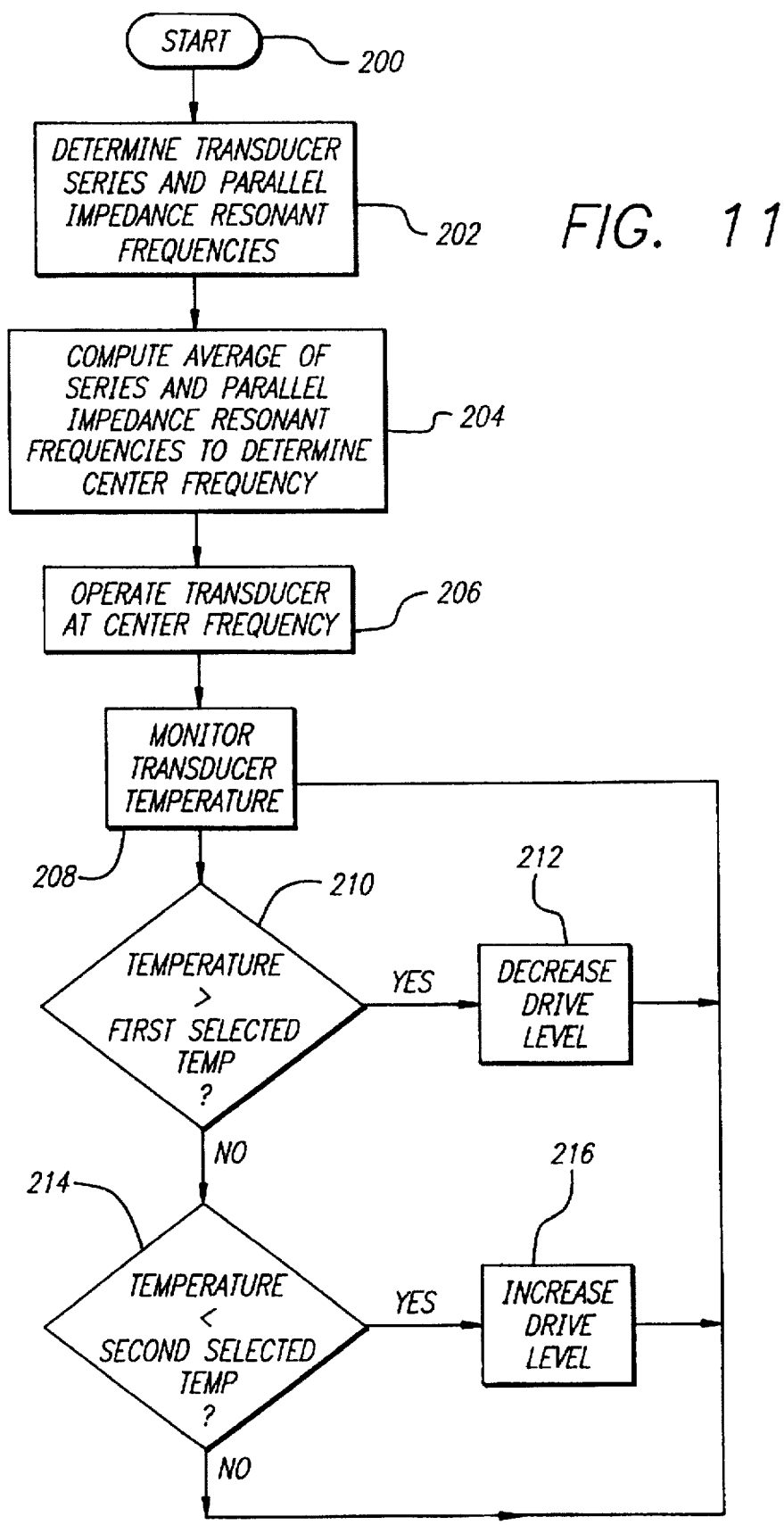
FIG. 11 is a flow chart illustrating a method for controlling the drive level in accordance with the present invention.

During the procedure shown in FIG. 11, the operating frequency is maintained constant at the center frequency established in step 106. Controlling the drive level as shown in FIG. 11 permits control over the temperature so that tissue charring and blood boiling can be avoided.

The above method specifically mentions sweeping and tuning the drive frequency at only one time, after introduction to the patient and when at the patient energy delivery site. However, the automatic tuning process can be conducted at other times also. For example, it may be automatically conducted while energy is being delivered. The control processor may automatically and periodically sweep the frequencies to determine the optimum operating for the crystal at any time, including when the application of power by the ultrasonic crystal has raised the site temperature to 85° C. or higher. This operation was not selected in the previously-discussed embodiment because it was found that with the bio-layer, even though the optimum operating frequency changed with temperature, there was so little loss of power transfer that it was deemed to be not necessary to re-tune or recalibrate the crystal. However, such periodic re-tuning or recalibration would be possible with the system and method presented above.

Additionally, the above embodiment has specifically mentioned the use of the average of the series and parallel frequencies as the operating frequency. However, a different operating frequency may be selected based on these detected frequencies or another detected frequency or frequencies. For example, where a higher Q crystal is needed for a particular application, the tuning system may be used to locate either the series or parallel frequency and operate at one of those frequencies or at a frequency that may be determined by reference to them. This frequency location and selection may be automatic as described above.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A system for delivering energy to biological tissue, comprising:

a catheter having distal and proximal ends;

an ultrasonic transducer adapted to transduce electrical energy into acoustic energy, the transducer having a characteristic frequency, the transducer mounted at the distal end of the catheter;

a power supply that provides electrical energy to the ultrasonic transducer at a selectable frequency;

a power transfer sensor coupled to the ultrasonic transducer that measures the response of the ultrasonic transducer to the power provided to it by the power supply, the sensor providing a power transfer signal;

a processor adapted to automatically control the power supply to vary the frequency of electrical energy applied to the transducer and to monitor the power transfer signal in response to the frequency variation to determine the characteristic frequency of the transducer.

2. The system of claim 1 wherein the processor automatically controls the power supply to sweep through a predetermined range of frequencies while monitoring the power transfer signal to determine the characteristic frequency.

3. The system of claim 2 wherein the processor automatically controls the power supply to operate at the determined characteristic frequency.

4. The system of claim 2 wherein the processor is adapted to automatically process the determined characteristic frequency to derive an operation frequency therefrom and automatically control the power supply to operate at the operation frequency.

5. The system of claim 1 wherein the tuning system automatically controls the power supply to sweep through a predetermined range of frequencies while monitoring the power transfer signal to determine first and second resonance frequencies of the ultrasonic transducer.

6. The system of claim 5 wherein the processor automatically controls the power supply to operate at or near one of the determined resonance frequencies.

7. The system of claim 5 wherein the tuning system automatically processes the determined resonance frequencies to derive an operation frequency therefrom and automatically controls the power supply to operate at the operation frequency.

8. The system of claim 7 wherein the processor automatically averages the first and second resonance frequencies and automatically controls the power supply to operate at the average frequency.

9. The system of claim 8 further comprising a power application switch;

wherein the processor is responsive to actuation of the power application switch to automatically control the power supply to apply power to the ultrasonic transducer while varying the frequency to determine the first and second resonant frequencies while monitoring the power transfer signal and to then apply a predetermined level of power as selected at the operation frequency.

10. The system of claim 1 further comprising a biologically-compatible layer formed on the outside of the ultrasonic transducer that lowers the frequency sensitivity of the transducer.

11. The system of claim 10 wherein the biologically-compatible layer is non-metallic and has a relatively high coefficient of thermal conductivity.

12. The system of claim 1 further comprising a temperature sensor mounted at the distal end of the catheter that senses temperature and provides a temperature sensing signal.

13. The system of claim 12 wherein the processor receives the temperature sensing signal, compares it to a predetermined first threshold temperature and controls the power supply to decrease the power drive level when the temperature signal represents a temperature above the first threshold.

14. The system of claim 13 wherein the processor automatically controls the power supply to hold the frequency constant while varying the power level to maintain the temperature within a predetermined range.

15. The system of claim 12 wherein the temperature sensor is mounted in the ultrasonic transducer.

16. The system of claim 15 wherein the ultrasonic transducer is cylindrically shaped.

17. A method of delivering energy to a biological site, comprising the steps of:

locating a catheter having an ultrasonic transducer at the site;

applying electrical power to the ultrasonic transducer that is adapted to transduce electrical energy into acoustic energy, the transducer having a characteristic frequency;

measuring the response of the ultrasonic transducer to the power provided to it, the sensor providing a power transfer signal;

automatically varying the frequency of electrical energy applied to the transducer and monitoring the power transfer signal in response to the frequency variation to determine the characteristic frequency of the transducer.

18. The method of claim 17 wherein the step of varying the frequency comprises the step of automatically sweeping through a predetermined range of frequencies while monitoring the power transfer signal to determine the characteristic frequency.

19. The method of claim 18 comprising the further step of automatically applying power to the transducer to operate at the determined characteristic frequency.

20. The method of claim 18 comprising the further step of automatically processing the determined characteristic frequency to derive an operation frequency therefrom and automatically applying power to the transducer at the derived operation frequency.

21. The method of claim 17 further comprising the step of automatically sweeping through a predetermined range of frequencies while monitoring the power transfer signal to determine first and second resonance frequencies of the ultrasonic transducer.

22. The method of claim 21 comprising the further step of automatically applying power to the transducer at or near one of the determined resonance frequencies.

23. The method of claim 21 comprising the further step of automatically deriving an operation frequency from the determined resonance frequencies and automatically applying power to the transducer to operate at the operation frequency.

24. The method of claim 23 comprising the step of averaging the first and second resonance frequencies and automatically applying power to the transducer to operate at the average frequency.

25. The method of claim 24 further comprising the steps of:

actuating a power application switch;

automatically applying power to the ultrasonic transducer while varying the frequency in response to actuation of the power application switch to determine the first and second resonant frequencies while monitoring the power transfer signal; and applying a predetermined level of power to the transducer at the operation frequency.

26. The method of claim 17 further comprising the step of forming a biologically-compatible layer on the outside of the ultrasonic transducer that lowers the frequency sensitivity of the transducer.

27. The method of claim 26 wherein the step of forming the biologically-compatible layer comprising forming the layer of a non-metallic material that has a relatively high coefficient of thermal conductivity.

28. The method of claim 17 further comprising the steps of sensing temperature at the distal end of the catheter and providing a temperature sensing signal.

29. The method of claim 28 further comprising the steps of comparing the temperature sensing signal to a predetermined first threshold temperature;

decreasing the power drive level to the transducer when the temperature signal represents a temperature above the first threshold.

30. The method of claim 28 further comprising the step os automatically controlling the frequency to be constant while varying the power level to maintain the temperature within a predetermined range.

31. The method of claim 28 further comprising the step of mounting the temperature sensor in the ultrasonic transducer.

32. The method of claim 31 comprising the step of forming the ultrasonic transducer to be cylindrical in shape.

* * * * *